United States Patent [19]

Wilson

[11] Patent Number: 4,577,543
[45] Date of Patent: Mar. 25, 1986

[54] CONSTRUCTION OF A MONOLITHIC REINFORCED CATHETER WITH FLEXIBLE PORTIONS

[75] Inventor: Bruce C. Wilson, Glens Falls, N.Y.

[73] Assignee: American Hospital Supply Corporation, Evanston, Ill.

[21] Appl. No.: 524,347

[22] Filed: Aug. 18, 1983

[51] Int. Cl.⁴ .................. D04C 1/06; A61M 25/00
[52] U.S. Cl. .................................... 87/11; 57/6; 57/7; 87/1; 87/6; 87/9; 138/123; 604/280; 604/282
[58] Field of Search ............ 87/5, 6, 7, 1, 9, 11, 87/13, 29, 30, 28, 34; 604/280-282; 57/6, 207, 7; 138/123, 125, 127

[56] References Cited

U.S. PATENT DOCUMENTS

| | | | |
|---|---|---|---|
| 2,223,954 | 12/1940 | Ford | 87/6 |
| 2,257,953 | 10/1941 | Haskell | 87/6 |
| 2,378,568 | 6/1945 | Merwin | 57/6 |
| 3,485,234 | 12/1969 | Stevens | 138/123 X |
| 3,924,632 | 12/1975 | Cook | 138/125 X |
| 3,938,313 | 2/1976 | Marzocchi | 57/207 |
| 3,944,453 | 3/1976 | Chudgar et al. | 138/125 X |
| 3,945,867 | 3/1976 | Heller, Jr. et al. | 138/123 X |
| 4,200,126 | 4/1980 | Fish | 138/127 X |
| 4,321,226 | 3/1982 | Markling | 264/139 |
| 4,326,905 | 4/1982 | Tanaka | 87/9 X |

Primary Examiner—John Petrakes
Attorney, Agent, or Firm—Cushman, Darby & Cushman

[57] ABSTRACT

A generally cylindrical member, such as a catheter, cannulae, or the like, has a monolithic construction. An inner core of plastic is passed through a conventional reinforcing apparatus, such as a conventional braiding mechanism. The braiding action is interrupted at predetermined intervals while the core continues to be fed so that straight reinforcing strand lengths are disposed on the outer surface of the inner core at predetermined lengths. The member passes through a heated sizing die to adhere the braided strand to the inner core, and a mechanical shear or rotating blade cuts the straight strand lengths off so that they are detached from the core. An over-extrusion of plastic may be provided to encapsulate the reinforcing strands. When the catheter is free of reinforcing strands it is relatively soft and flexible—such as at its tip—and where the reinforcing strands are provided it is relatively stiff. The monolithic construction ensures that components will not detach in a patient's body.

10 Claims, 7 Drawing Figures

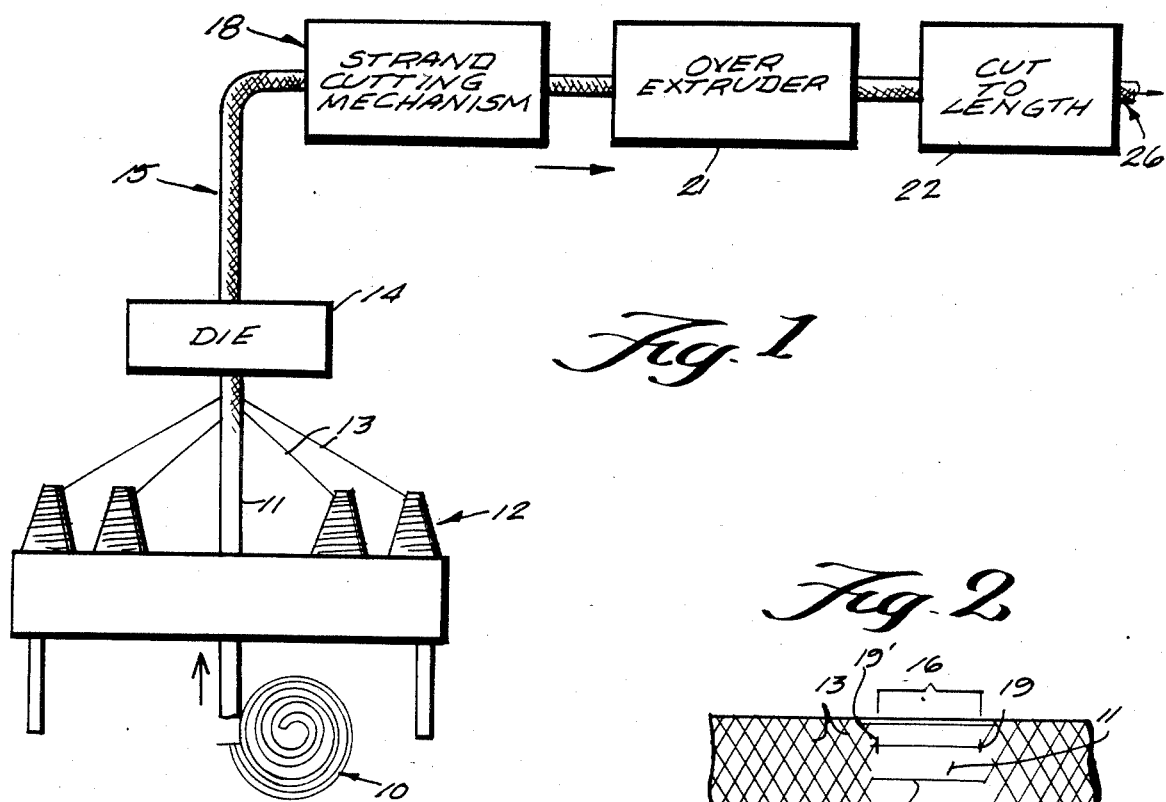
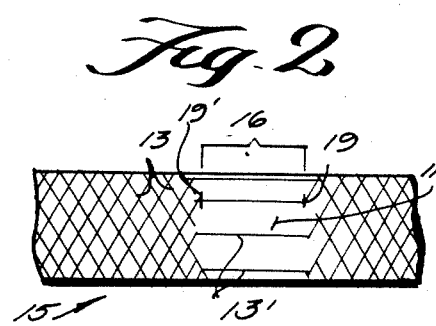
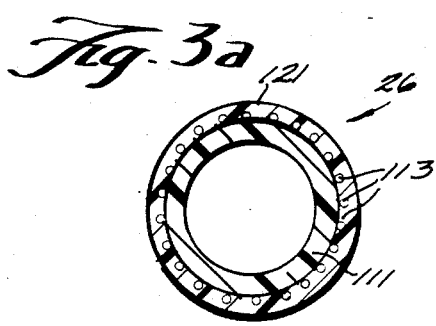
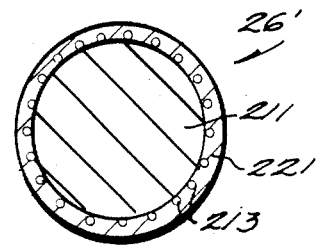
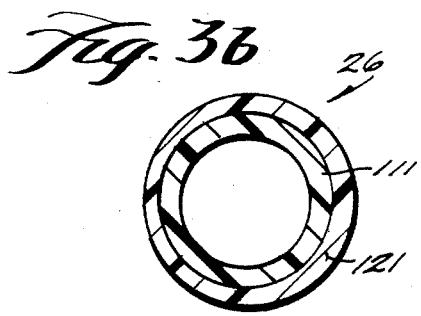
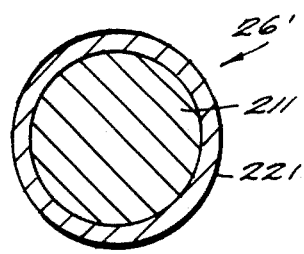
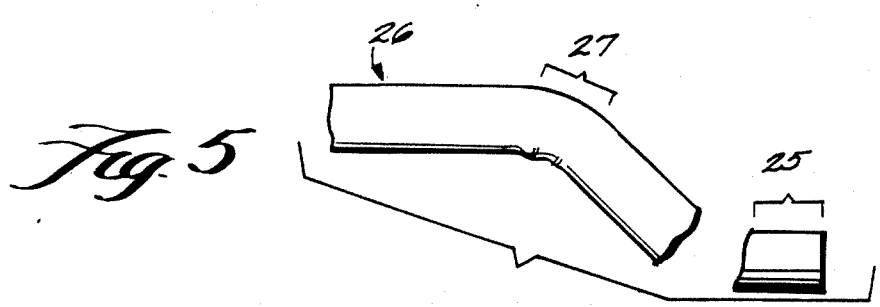

CONSTRUCTION OF A MONOLITHIC REINFORCED CATHETER WITH FLEXIBLE PORTIONS

BACKGROUND AND SUMMARY OF THE INVENTION

The invention relates, in general, to the construction of relatively flexible elongated generally cylindrical members having reinforcing material in association with a substantial length of the cylindrical members to make the reinforced portions significantly less flexible than portions not having the reinforcing material associated therewith. In particular, the invention relates to catheters and the like, and methods of construction thereof, wherein a monolithic body has reinforcing material disposed in association with a portion thereof to render it less flexible than it inherently is, with the reinforcing material interrupted so that it does not extend for the entire length. The term "monolithic" as used in the present specification and claims means completely integral, as opposed to two-piece constructions which are common in the prior art.

In the construction of catheters for many functions, particularly electrode catheters or catheters used to inject radiopaque materials into body structures, it is essential that some portions of the catheter be soft and flexible. However, in order to properly position the catheter in the patient's body, it is necessary for other portions of the catheter to be stiff. These two conflicting requirements are usually accommodated in the prior art by making the tip of the catheter (and/or portions thereof that must be bent significantly in use or in insertion) so that it is soft and flexible, while the rest of the catheter is stiff. For instance U.S. Pat. No. 3,485,234 to Stevens shows a typical prior art catheter, and method of construction thereof, wherein a portion of a reinforced catheter body is ground off to expose a small portion of the wire braid reinforcement, and a separate and distinct tip of flexible material is slipped over the ground off end and fused to the catheter body by heat and pressure. Catheters constructed in this manner are not entirely suitable since the parts that are fused together can disassociate within the patient's body, with disastrous consequences, and additionally such catheters are relatively difficult to produce. In U.S. Pat. No. 4,321,226 it is suggested that a tubular catheter can be constructed by applying the reinforcing material to the entire catheter body, and after application to the catheter body selectively grinding off portions of the reinforcement. This procedure is relatively difficult to implement, and results in disruption of the reinforcement and marring of the core and results in surfaces that are not in dimensional tolerance and are not smooth. Even when an over-extrusion is applied the catheter may not have the desired dimensional tolerance or smoothness.

These disadvantages of prior art catheters, and methods of construction, are avoided by providing a monolithic construction according to the present invention.

According to one aspect of the present invention, a generally cylindrical member, such as (but not restricted to) a catheter, cannulae, or the like, is provided consisting of a relatively flexible elongated monolithic generally cylindrical body, and reinforcing material in association with a significant length of the cylindrical body, the reinforcing material making the body portions with which it is associated significantly less flexible, but a portion of the monolithic body being free of reinforcing material and thus retaining its relative flexibility. The cylindrical body may be hollow (e.g. a biological catheter) or solid (e.g. an electrode catheter), and preferably is made of a bio-compatible thermoplastic material.

The reinforcing material preferably comprises strands wrapped around the circumference of an inner core portion of the cylindrical body. Typical materials of which the strand may be formed include metal wire (e.g. steel wire), or synthetic fibers (e.g. fiberglass or aramid). The wrapping of the body by the strands may be accomplished by braiding, helical wrapping, or in a wide variety of other conventional reinforcing manners.

While any portion along the length of the member may be free of reinforcing material, for many medical uses it is desirable that the tip of the member be relatively soft and flexible, and thus the tip portion is free of reinforcing material.

According to another aspect of the present invention, a method is provided for constructing a reinforced monolithic elongated generally cylindrical member. The method comprises the steps of: (a) Forming a generally cylindrical monolithic body of relatively soft material, so that the body is relatively flexible; and (b) Disposing reinforcing material in operative association with a portion, but not all, of the body along the length thereof, so that where the reinforcing material is applied the member constructed is significantly less flexible than the body, but where the reinforcing material is not applied the member retains substantially the same flexibility as the body. Step (a) of the method according to the invention may be practiced by forming either a hollow or solid core of thermoplastic material, and step (b) is practiced by passing the inner core through a conventional reinforcement wrapping (e.g. braiding) machine. The wrapping operation is terminated at predetermined intervals for predetermined periods of time, and while the wrapping operation is terminated the body is continuously fed so that straight lengths of reinforcing strands are disposed on the periphery of the body. The body, with reinforcing strands, passes through a heated die so that the wrapped strands (e.g. braids) adhere to the surface of the body, but the straight portions do not. The straight portions then pass through a strand cutting mechanism, such as a mechanical cutting mechanism, at which point the straight portions are cut off. The member may then pass to an over extruder, and eventually is cut to length, the reinforcement-free portions of the monolithic catheter produced providing the desired flexibility for use and/or insertion of the catheter, and/or providing a tip portion that will not damage internal organs or the like. The member is produced without the necessity of forming the reinforcement braids over the entire length with subsequent grinding off of the unused portions.

It is the primary object of the present invention to provide a simple and effective generally cylindrical member, and method of construction thereof, having a relatively flexible elongated monolithic generally cylindrical body with reinforcing material disposed in operative association with a portion, but not all, of the length of the member. This and other objects of the invention will become clear from an inspection of the detailed description of the invention, and the appended claims.

BRIEF DESCRIPTION OF THE DRAWINGS

FIG. 1 is a schematic view illustrating exemplary apparatus for practicing an exemplary method of producing a cylindrical member according to the present invention;

FIG. 2 is a side view of a particular portion of a production intermediate produced utilizing the apparatus of FIG. 1, just prior to feeding of the member into the strand cutting mechanism;

FIGS. 3a and 3b are cross-sectional views of an exemplary biological catheter produced according to the method of the present invention, FIG. 3a taken at a reinforced portion of the catheter, and FIG. 3b taken at a reinforcement-free portion of the catheter;

FIGS. 4a and 4b are cross-sectional views comparable to those of FIGS. 3a and 3b only illustrating an exemplary electrode catheter produced according to the method of the present invention; and FIG. 5 is a partial side view of a final exemplary catheter produced according to the method of the present invention.

DETAILED DESCRIPTION OF THE DRAWINGS

FIG. 1 illustrates exemplary apparatus for practicing a method of constructing a catheter, or the like, according to the present invention. While the invention will be particularly described with respect to construction of the catheter, it is understood that the invention is equally applicable to the construction of other generally cylindrical members which, in use, require the monolithic, interrupted reinforcement, construction of the members according to the present invention.

In the practice of an exemplary method utilizing the apparatus of FIG. 1, a flexible body 11 of relatively soft material, such as a tube or solid cylinder of thermoplastic material, is fed from a coil 10 upwardly through a conventional reinforcement applying apparatus 12. An interior supporting structure may be used interior of the body when tubular.

The apparatus 12 preferably comprises an apparatus for wrapping strands of reinforcing material around the circumference of the body 11. For instance the apparatus 12 may comprise a conventional braiding machine, such as shown in U.S. Pat. Nos. 4,200,126, and 4,326,905. Typically, a frame of the braiding apparatus 12 rotates around the upwardly fed body 11 to provide the braiding action, and the braiding action may be terminated when desired by stopping rotation of the braiding apparatus while continuing feed of the body 11. The body 11 typically will have a circular cross-section, although depending upon the use may have a wide variety of other cross-sections that are capable of having reinforcing material applied thereto.

The apparatus 12 preferably wraps strands 13 of reinforcing material around the circumference of the body 11. The strands 13 may be of any conventional reinforcing material such as metal (e.g. steel) wire, synthetic fibers (fiberglass, aramid, etc.), or the like. After the reinforcing strands 13 are applied the upwardly moving body 11 passes through a conventional heated sizing die 14 or the like, the die causing the body 11 to become tacky so that the braided strands 13 are held in place thereon. A geared wheel above the die 14 provides the necessary force for continuously moving the body 11 upwardly, and the intermediate member 15 that is produced may be wound up into a coil before further processing.

In order to provide interruptions of the reinforcement along the length of the catheter being produced, periodically the rotation of the braiding apparatus 12 is interrupted, while the upward movement of the body 11 continues. This results in the formation of substantially straight lengths 13' of the braided strands 13 along the length of the intermediate member 15, as seen in FIG. 2. That is, the portion 16 of the intermediate member 15 is formed during the time interval that rotation of the braiding apparatus 12 is interrupted. The straight strand lengths 13' do not have a tendency to adhere to the body 11 when passing through the heated die 14.

The intermediate member 15, after construction thereof, is fed to the strand cutting mechanism 18. The strand cutting mechanism 18 may be any conventional cutting apparatus or may comprise a manual cutting station. Typically, a mechanical shear or rotating blade would automatically be moved into operative association with the straight strand lengths 13' to effect cutting. For instance, the shear or blade would be moved into contact with the straight strand lengths 13' at the ends 19, 19' (see FIG. 2) of each. These straight strand lengths 13' would fall off, or be rubbed off, the body 11, while the braided strands 13 on either side thereof would be unaffected and would continue to adhere to the body 11.

After passing through the strand cutting mechanism 18, the member 15 optionally may pass to over extruder 21 or the like, at which point another layer of thermoplastic material would be applied to the entire body 15 (both the braided and reinforcement-free portions thereof) The over-extruder is not necessary, however, since the catheter body is relatively smooth after passage through die 14 and cutter 18. Instead of an over extruder 21, some other mechanism or procedure may be utilized to provide an outer sleeve to the member 15, the over extruded plastic or the outer sleeve essentially encapsulating the reinforcing braids 13. The end product (26) that results is a completely monolithic member with spaced interrupted portions.

Whether or not the over-extruder 21, or like mechanism, is utilized to provide an outer sleeve or extrusion of material on the member 15, the member is ultimately cut to length, as at station 22 (see FIG. 1). The cuts are made, utilizing conventional cutting equipment, in order to construct a member having a reinforcement-free portion(s) (e.g. 16) thereof at a predetermined position(s) therealong. For instance, in the construction of exemplary catheters according to the present invention, at station 22 the cutting operation will be practiced so that the tip portion 25 (see FIG. 5) of the catheter 26 that is produced is reinforcement-free, and if desired one or more reinforcement-free portions 27 may be disposed along the length thereof to accommodate desired bending of the catheter 26 during use and/or insertion.

FIG. 3a shows a typical cross-section of a reinforced portion of an exemplary catheter 26 produced according to the method of the present invention. The catheter 26 includes a hollow inner body 111, with reinforcement strands 113 braided on the periphery thereof, and an over-extrusion 121 encapsulating the strands 113. In FIG. 3b the cross-section of the same catheter 26 is taken at a reinforcement-free portion thereof (e.g. tip portion 25 for the cathether illustrated in FIG. 5). Here there are no reinforcing strands 113, therefore the catheter 26 is relatively flexible and soft at that portion, rather than being stiff as at the portions where the reinforcing strands 113 are provided.

The catheter 26' illustrated in FIGS. 4a and 4b is substantially identical to the catheter 26 illustrated in FIGS. 3a and 3b except that it is an electrode catheter so that the inner body 211 is solid, with reinforcing strands 213 surrounding it and an optional over-extrusion 221 encapsulating the strands 213.

It will thus be seen that the catheter 26 produced according to the method of the present invention has the requisite stiff and flexible portions to provide both ease of insertion yet safe and effective use. For instance the great majority of the body of the catheter 26 has reinforcing braids 13 applied, so that it is stiff, yet the tip portion 25, and/or other portions thereof, are relatively flexible and soft so that damage to internal organs is avoided, and proper positioning of the catheter is facilitated. The catheter 26 produced according to the method of the invention has a smooth exterior, and monolithic construction so that it is impossible for portions thereof to detach during use in the patient's body. A catheter according to the invention may be produced by fewer, and less difficult, procedures than the segmented catheters or other monolithic catheters of the prior art.

While the invention has been presently illustrated and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent structures and procedures.

What is claimed is:

1. A method of constructing a selectively reinforced monolithic elongated generally cylindrical catheter, comprising the steps of:
   (a) forming a relatively flexible elongated generally cylindrical body of relatively soft material by forming an inner core of thermoplastic material; and
   (b) disposing reinforcing material in operative association with a part, but not all, of said body so that where the reinforcing material is disposed the body has significantly less flexibility, and where the reinforcing material is not disposed the body is relatively flexible, by: (i) passing said inner core through a reinforcement material wrapping apparatus; (ii) periodically interrupting wrapping action of the wrapping apparatus while continuing to pass the inner core therethrough so as to form relatively straight strand portions along the length of the outer surface of the inner core, and then restarting the wrapping action of the wrapping apparatus; and (iii) cutting off the relatively straight strand portions on the circumference of the inner core to provide the reinforcement-free, relatively flexible, portions of the monolithic catheter.

2. A method as recited in claim 1 wherein step (a) is practiced by forming a hollow core.

3. A method as recited in claim 1 wherein step (a) is practiced by forming a solid core.

4. A method as recited in claim 1 wherein the wrapping of step (b) is practiced by braiding strands of reinforcing material around the circumference of said inner core.

5. A method as recited in claim 1 comprising the further step of, prior to substep (iii) and after substep (ii), passing the inner core through a heated die so as to cause adherence of the wrapped portions, but not the relatively straight portions, of the strands to the inner core.

6. A method as recited in claim 5 wherein the wrapping of step (b) is practiced by braiding strands of reinforcing material around the circumference of said inner core.

7. A method as recited in claim 5 wherein substep (iii) is practiced by passing the inner core into operative association with a mechanical shear or a rotating cutting blade.

8. A method as recited in claim 1 comprising the further step of (c) over-extruding thermoplastic material over said inner core to encapsulate strands of reinforcing material where they exist, and to surround said inner core over essentially the entire length thereof.

9. A method as recited in claim 1 wherein substep (iii) is practiced by passing the inner core into operative association with a mechanical shear or a rotating cutting blade.

10. A method as recited in claim 1 consisting of steps (a) and (b), and the step of cutting the member to length.

* * * * *